(12) United States Patent
Nagler et al.

(10) Patent No.: US 12,420,972 B2
(45) Date of Patent: Sep. 23, 2025

(54) SYSTEM FOR TRANSPORTING LOOSE STERILE CLOSURE ELEMENTS

(71) Applicant: Syntegon Technology GmbH, Waiblingen (DE)

(72) Inventors: Stefan Nagler, Unterschneidheim (DE); Ulrich Krauß, Ilshofen (DE); Markus Ilgenfritz, Feuchtwangen (DE); Albrecht Kühnle, Crailsheim (DE)

(73) Assignee: Syntegon Technology GmbH, Waiblingen (DE)

( * ) Notice: Subject to any disclaimer, the term of this patent is extended or adjusted under 35 U.S.C. 154(b) by 241 days.

(21) Appl. No.: 18/262,424

(22) PCT Filed: Jan. 20, 2022

(86) PCT No.: PCT/EP2022/051178
§ 371 (c)(1),
(2) Date: Jul. 21, 2023

(87) PCT Pub. No.: WO2022/157219
PCT Pub. Date: Jul. 28, 2022

(65) Prior Publication Data
US 2024/0083615 A1  Mar. 14, 2024

(30) Foreign Application Priority Data
Jan. 22, 2021 (DE) .................. 10 2021 101 384.4

(51) Int. Cl.
*B65B 55/02* (2006.01)
*B65B 7/28* (2006.01)
(Continued)

(52) U.S. Cl.
CPC .......... *B65B 55/027* (2013.01); *B65B 7/2807* (2013.01); *B65B 37/04* (2013.01);
(Continued)

(58) Field of Classification Search
CPC ..... B65B 55/027; B65B 7/2807; B65B 37/04; B65B 37/10; B65B 3/006; B65B 37/02;
(Continued)

(56) References Cited

U.S. PATENT DOCUMENTS 2,696,285 A   12/1954  Zenlea
3,086,639 A    4/1963  Donofrio
(Continued)

FOREIGN PATENT DOCUMENTS

AU       491985 B2   6/1977
DE   202005002903 U1   9/2005
(Continued)

OTHER PUBLICATIONS

EPO translation of FR 2866016 (Year: 2025).*
(Continued)

*Primary Examiner* — Mark A Deuble
(74) *Attorney, Agent, or Firm* — Michael Best & Friedrich LLP

(57) ABSTRACT

The invention relates to a system (10) for transporting loose sterile closure elements (12) from the surroundings (14) of an isolator (16) into an interior (18) of the isolator, comprising a container (24) for storing a stock quantity of closure elements in the surroundings of the isolator, an isolator opening (20) and a collecting device (56) for collecting the closure elements and for providing the closure elements in the interior of the isolator, with a metering device (46) for controlling a target quantity of closure elements to be transported from the container through the isolator opening and into the collecting device.

18 Claims, 15 Drawing Sheets

(51) Int. Cl.
*B65B 37/04* (2006.01)
*B65B 37/10* (2006.01)
*B65G 47/14* (2006.01)
*B65G 47/19* (2006.01)

(52) U.S. Cl.
CPC .......... *B65B 37/10* (2013.01); *B65G 47/1428* (2013.01); *B65G 47/1457* (2013.01); *B65G 47/19* (2013.01)

(58) Field of Classification Search
CPC ................ B65G 47/1428; B65G 47/1457; B65G 47/19; B65G 65/23; A61L 2202/123; A61L 2/26
See application file for complete search history.

(56) References Cited

U.S. PATENT DOCUMENTS

| | | | | |
|---|---|---|---|---|
| 5,302,073 | A * | 4/1994 | Riemersma | B65G 65/23 414/292 |
| 5,447,699 | A | 9/1995 | Papciak et al. | |
| 5,685,454 | A * | 11/1997 | Bonerb | B65D 88/56 383/906 |
| 6,254,330 | B1 * | 7/2001 | Steffen | B65G 65/23 141/285 |
| 7,118,319 | B1 * | 10/2006 | Debrunner | B65G 65/23 414/421 |
| 7,828,135 | B2 | 11/2010 | Fischer et al. | |
| 9,637,261 | B2 * | 5/2017 | Monti | B65B 55/12 |
| 2024/0076085 | A1 * | 3/2024 | Eßling | A61L 2/22 |

FOREIGN PATENT DOCUMENTS

| | | |
|---|---|---|
| DE | 102016004200 A1 | 10/2017 |
| DE | 102019007042 A1 | 4/2021 |
| EP | 1510227 A1 | 3/2005 |
| EP | 3613442 A1 | 2/2020 |
| FR | 2866016 A1 | 8/2005 |
| WO | 2004042381 A2 | 5/2004 |

OTHER PUBLICATIONS

Opposition Decision for German Application No. 102021101384.4 dated for Nov. 23, 2023 (26 pages including English translation).
German Patent Office Action for Application No. 102021101384.4 dated Sep. 15, 2021 (7 pages including statement of relevance).
Translation of International Search Report for Application No. PCT/EP2022/051178 dated May 6, 2022 (3 pages).
Opposition for German Application No. 102021101384.4 dated Nov. 29, 2022 (25 pages including English translation).
Response to Opposition for German Application No. 102021101384.4 dated Mar. 28, 2023 (37 pages including English translation).
Summons to Oral Proceedings for German Application No. 102021101384.4 dated Jul. 24, 2023 (9 pages, statement of relevance included).

* cited by examiner

SYSTEM FOR TRANSPORTING LOOSE STERILE CLOSURE ELEMENTS

BACKGROUND

The invention relates to a system known from EP 3 613 442 A1 for transporting loose sterile closure elements from an environment of an isolator into an interior of the isolator, comprising a receptacle for storing a stock quantity of closure elements in the environment of the isolator, an isolator opening, and a collecting device for collecting the closure elements and for providing the closure elements in the interior of the isolator.

The space available within an isolator is inherently limited. It is therefore desirable to use this space as productively as possible, i.e., in particular for handling a closure element and positioning it at or on a vessel which is arranged inside the isolator and which is filled and is to be closed.

SUMMARY

The present object is to make available a system for transporting loose sterile closure elements, which system enables the interior of the isolator to be used as productively as possible.

In a system of the type mentioned at the outset, this object is achieved by a metering device for controlling a target quantity of closure elements to be transported from the receptacle through the isolator opening and into the collecting device.

According to the invention, the closure elements can be stored essentially outside the isolator, while only a comparatively small target quantity of closure elements is supplied to the collecting device arranged inside the isolator. The metering of the closure elements makes it possible to use the interior of the isolator as productively as possible, for example for closing receptacles with closure elements. The metering device ensures reliable replenishment for the productive utilization of the interior of the isolator, in particular autonomously and independent of operating personnel.

The target quantity transported is defined by an absolute quantity of closure elements (e.g., "20 items") or by an absolute quantity of closure elements related to a unit of time (e.g., "20 items per minute" or "1 item every 3 seconds").

In a preferred embodiment, the metering device has at least one actuator which can be switched between a resting state and a use state depending on the target quantity to be transported. It is conceivable that the actuator is permanently active during productive operation of the isolator and that closure elements are transported from the receptacle into the collecting device at a predefinable frequency (quantity per time). However, it is also conceivable that the actuator is brought to a use state intermittently and that closure elements are transported in batches, for example with supply of a target quantity of X closure elements, subsequent interruption, and then subsequent supply of a further target quantity of X or Y closure elements.

The use state of the actuator is preferably associated with an increase in the potential and/or kinetic energy of at least a subset of the stock quantity of the closure elements. It is thus possible to bring the entire stock quantity of the receptacle to a higher energy state, or only a subset of the stock quantity.

A support arranged in the environment of the isolator, i.e., outside the isolator, is preferably provided for the receptacle, the at least one actuator changing the inclination and/or a vibrational state of the support and of the receptacle. For example, starting from a flat spatial position, a receptacle can be inclined such that the closure elements arranged within the receptacle are shifted farther upward in relation to the direction of gravity and from there can fall or slide downward following the direction of gravity. In a corresponding manner, it is possible to move a receptacle with closure elements, starting from a more inclined position, back to a flatter position, in order to inhibit or stop the tendency of the closure elements to fall or slide downward.

It is also possible for the support to interact with a vibration device, which brings the receptacle and the closure elements stored therein to a state of vibration. This state of vibration can have a movement component directed in the direction of the receptacle opening, such that the closure elements are stimulated to leave the receptacle and to be transported in the transport direction through the isolator opening into the collecting device.

The receptacle is preferably designed as a bag or as a container. These receptacles serve to transport already sterilized closure elements and can be made available in the environment of an isolator. It is known to dock such receptacles to rapid transfer ports (RTP) of an isolator, with a double door being used in the region of the isolator opening. A first part of such a double door is assigned to the isolator (as an "alpha part"). A second part of such a double door is provided by a receptacle closure/lid of the receptacle (as a "beta part"), said two parts of the double door being able to be mechanically coupled to each other so that these two parts together form a double door which, in a opened state, frees an isolator opening through which closure elements can be transported from the receptacle into the interior of the isolator.

It is also preferred if the metering device comprises at least one conveyor unit with a conveyor chamber whose volume is greater than the volume of an individual closure element and preferably smaller than the volume of two closure elements. A conveyor chamber of this kind enables individual metering of closure elements. For particularly gentle transport of the closure elements, it is preferred if the conveyor chamber increases in volume along a transport direction of the closure elements.

In a preferred embodiment of a conveyor unit, a conveyor drum is provided which forms an outer boundary of the conveyor chamber relative to a transport axis of the closure elements. Such a conveyor drum thus encloses at least part of the transport path of the closure elements.

It is possible for the conveyor drum to have at least one conveyor drum section which can be arranged or is arranged at the level of the isolator opening and covers a boundary of the isolator opening, such that closure elements to be transported cannot come into contact with the boundary of the isolator opening.

For gentle and simple transport of the closure elements, it is also preferred if the conveyor drum, relative to a transport axis of the closure elements, has a hollow-cylindrical portion and/or if the conveyor drum widens in the form of a hollow cone as seen in the transport direction of the closure elements.

It is also preferred if the conveyor unit has at least one conveyor element which delimits the conveyor chamber as seen along a transport axis of the closure elements. The at least one conveyor element serves to separate a plurality of closure elements. A conveyor element can be designed, for example, in the form of a guide web, a conveyor spiral or screw or a conveyor wheel.

It is also preferred if the metering device comprises a conveyor drive device, which can be switched depending on the target quantity to be transported, for rotating the conveyor drum and/or the conveyor elements. This conveyor drive device can be operated continuously or intermittently.

It is also possible that the metering device comprises a receptacle drive device for rotating the receptacle or a section of the receptacle about a central receptacle axis. In this way too, the state of movement of the closure elements within the receptacle or within a section of the receptacle can be stimulated. This stimulation can take place outside the isolator or else in the region of a section of the receptacle arranged within the isolator.

A section of the receptacle arranged within the isolator preferably has an outlet opening, the cross section of the latter being dimensioned such that a maximum of one closure element can be transported through this outlet opening at the same time.

It is possible that the metering device comprises a closure element line which has a bridging portion which can be arranged or is arranged within the isolator opening. The bridging portion covers a boundary of the isolator opening, such that closure elements to be transported cannot come into contact with the boundary of the isolator opening. A closure element line can be formed by a rigid line (for example by a pipe) or by a flexible line (for example by a hose).

In a particularly preferred embodiment, the metering device comprises a counting device for detecting a number, a weight and/or a volume of the closure elements, the counting device preferably being arranged upstream of the collecting device as seen in the transport direction of the closure elements. Such a counting device enables the formation of a control system and the detection of an actual quantity of closure elements, which can be compared against a predetermined target quantity of closure elements. An above-described actuator and/or a conveyor drive device and/or a receptacle drive device can then be controlled as a function of a difference between the predetermined target quantity and the detected actual quantity of closure elements.

To further increase productivity, it is preferred if the metering device or parts of the metering device is or are provided as an assembly that is movable within the isolator, which assembly is positionable preferably by means of a robot arm. The assembly comprises, for example, one or more of the following components, the function of which has already been described above. These are in detail: The conveyor unit (with a conveyor drum and/or at least one conveyor element) and/or the conveyor drive device and/or the receptacle drive device (in the case where the latter is arranged within the isolator) and/or the counting device and/or the closure element line.

In a preferred embodiment, the collecting device is designed as a sorting device, with preferably no buffer store for closure elements being connected upstream of the sorting device within the isolator. In particular, a comparatively small sorting device with a limited capacity (for example a maximum of 50 closure elements or in particular a maximum of 20 closure elements) can be used. There is no buffer store (also referred to as a "bunker") provided inside the isolator; the additional space thereby available in the interior is used for the producing components of the isolator.

BRIEF DESCRIPTION OF THE DRAWINGS

Further features and advantages of the invention are the subject matter of the following description and of the graphic illustration of preferred exemplary embodiments.

In the drawing.

DETAILED DESCRIPTION

Figure 1:
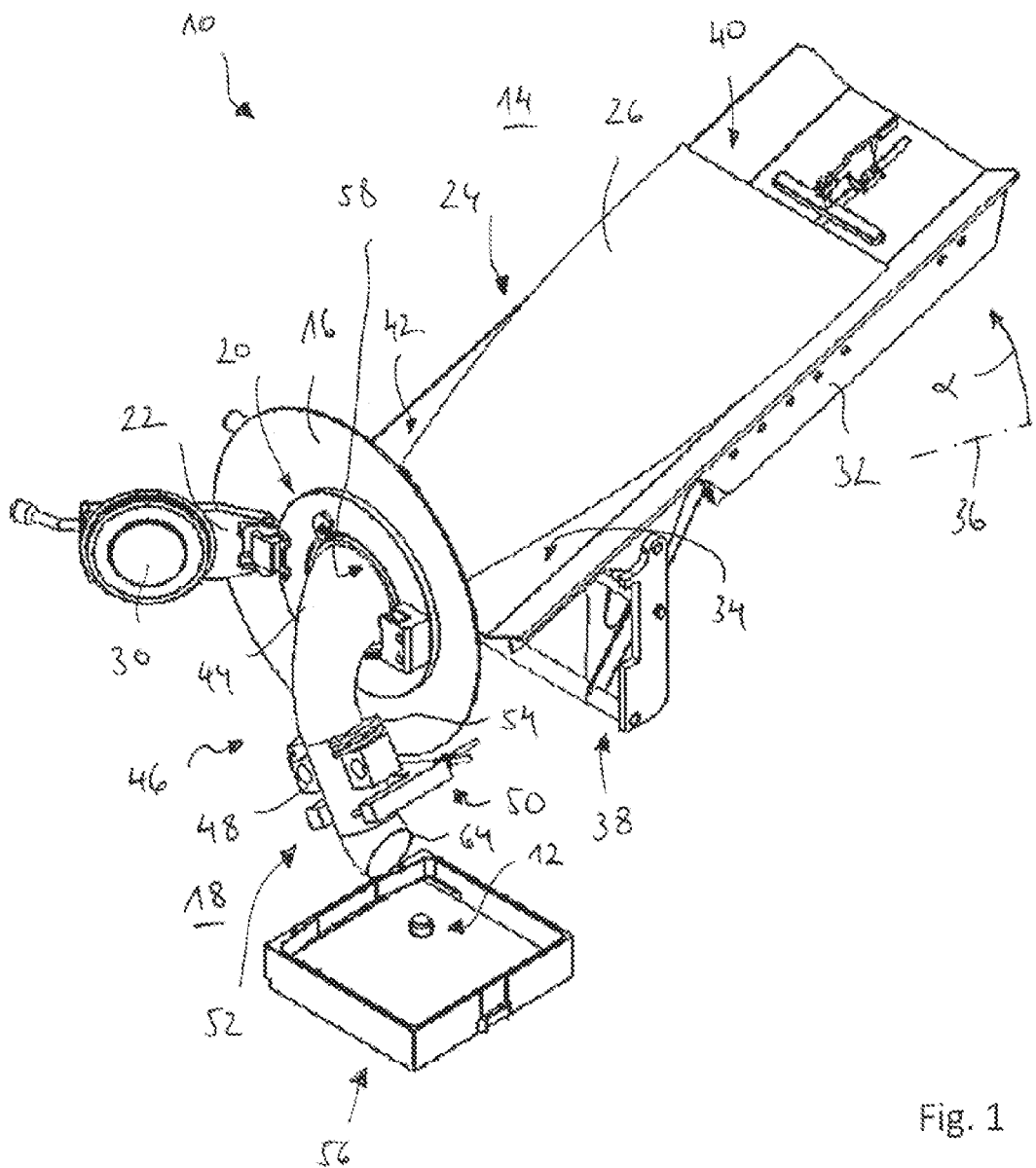
FIG. 1 shows a perspective view of a first embodiment of a system for transporting loose sterile closure elements, the system comprising a support, adjustable in inclination, for a receptacle in the form of a bag.

A system for transporting loose sterile closure elements is shown in the drawing and designated overall by reference sign 10. FIG. 1 shows an example of a closure element 12 which can be designed, for example, as a cap or plug and which serves as a closure for a vessel (for example a syringe) that is to be closed.

The system 10 serves to transport such closure elements 12 from an environment 14 of an isolator 16 into an interior 18 of the isolator.

The isolator 16 is shown only in part, specifically in the region of an isolator opening 20 which can be closed with an isolator door 22.

Figure 2:
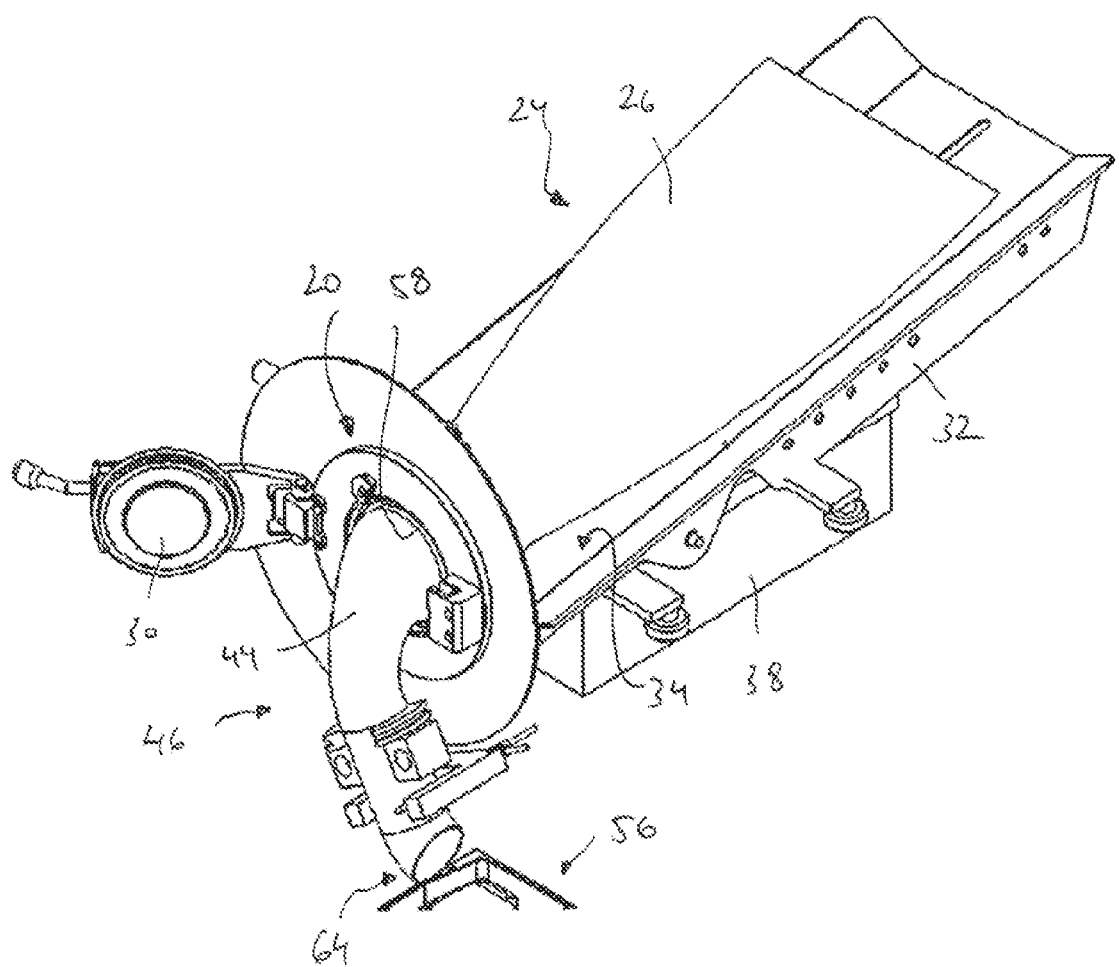
FIG. 2 shows a perspective view of a further embodiment of a system for transporting loose sterile closure elements, the system comprising a vibration support for a receptacle in the form of a bag.
Figure 3:
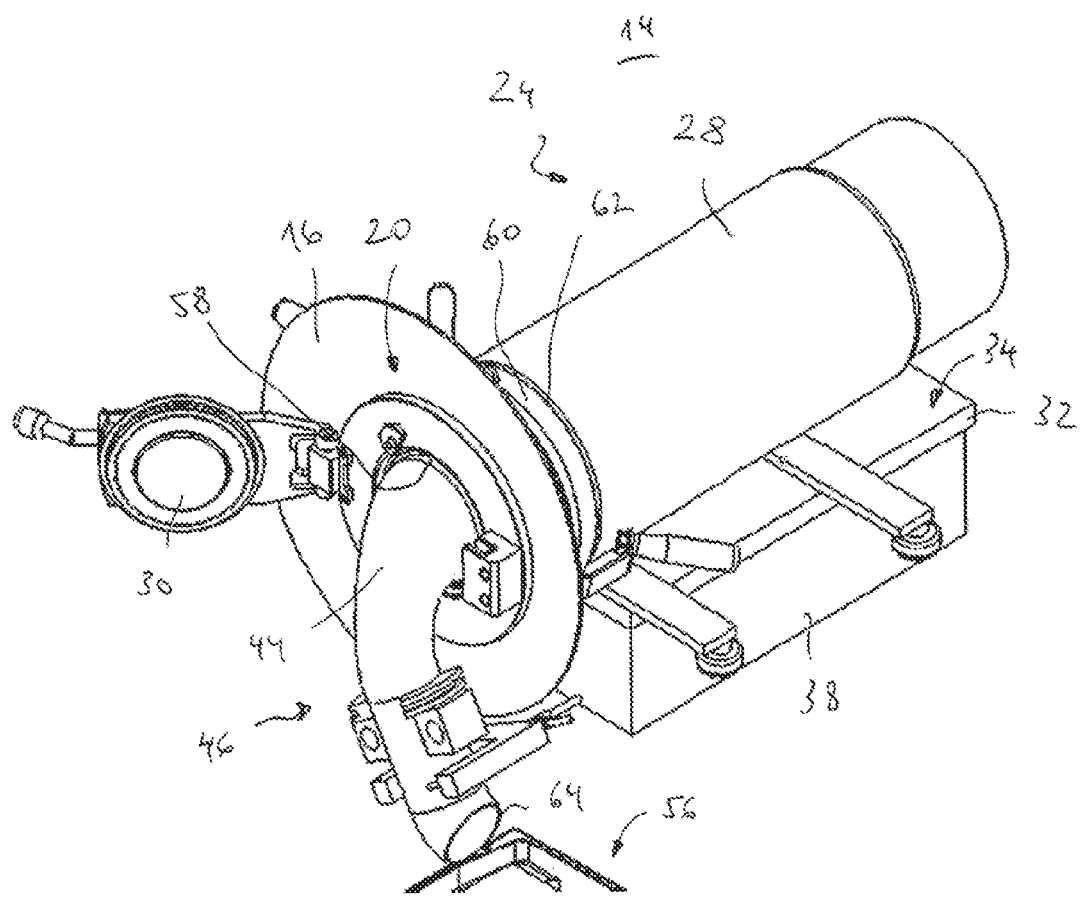
FIG. 3 shows a perspective view of a further embodiment of a system for transporting loose sterile closure elements, the system comprising a vibration support for a receptacle in the form of a container.

A receptacle 24 is provided for storing closure elements 12 in the environment 14 of the isolator 16, which receptacle 24 is designed in particular in the form of a bag 26 (see FIGS. 1 and 2) or a container 28 (see FIG. 3).

Irrespective of the configuration of the receptacle 24, such receptacles 24 can have a receptacle closure 30, which closes the receptacle 24 when the latter is in a delivery state. In such a delivery state, the isolator door 22 closes the isolator opening 20 of the isolator 16.

The receptacle 24 is then positioned with its receptacle closure 30 adjacent to the isolator door 22, so that, initially still in the environment 14 of the isolator 16, the isolator door 22 can be coupled mechanically to the receptacle closure 30. The receptacle 24 has an edge section which surrounds the receptacle closure 30 in a ring shape and which remains in the environment 14 of the isolator 16. When the isolator door 22 is opened, the receptacle closure 30 is detached from the receptacle 24 and is brought together with the isolator door 22 into the interior 18 of the isolator 16. Such a construction is also referred to as a "double door" of a "rapid transfer port".

The system 10 further comprises a support 32 arranged in the environment 14 of the isolator 16 and having a support surface 34 for supporting a receptacle 24.

In an initial state or resting state, the support surface 34 can extend for example in a horizontal plane 36. The inclination of the support 32 and thus of the support surface 34 according to an angle of inclination a is adjustable by means of an actuator 38. A greater inclination correlates with a greater height difference between a rear end 40 of the receptacle 24 and an end 42 of the receptacle 24 facing the isolator 16. As a result of the increase in the inclination of the support surface 34, the receptacle 24 and thus the closure elements 12 also stored in the receptacle 24 are transferred to a state with higher potential energy.

As soon as a resistance to slipping between closure elements 12 adjacent to one another and/or between the closure elements 12 and an inner wall of the receptacle 24 is overcome, the closure elements 12 emerge, assisted by gravity, from the receptacle 24 and pass into a closure element line 44 which is arranged in the interior 18 of the isolator and which is arranged such that a bridging portion 58 facing the receptacle 24 is arranged inside the isolator opening 20. The bridging portion 58 extends through the isolator opening 20 such that contact between the closure elements 12 to be transported and a potentially non-sterile boundary of the isolator opening 20, also referred to as a "ring of concern", is avoided.

The closure element line 44 is part of a metering device designated overall by the reference sign 46. This metering device 46 optionally comprises further components, for example a holder 48 connected to the closure element line 44 and/or a counting device 50 for detecting a number of closure elements 12 which pass through the closure element line 44. The holder 48 serves to fasten the metering device 46 to a mount (not shown) that is fixed to the isolator.

The closure element line 44, the holder 48 and the counter 50 can be provided as an assembly 52, which is manipulated either manually or, preferably, with the aid of a manipulation section 54 of the assembly 52, which can be coupled to the effector region of a robot arm. In this way, the metering device 46 can be removed from a region adjacent to the isolator opening 20, for example in order to close the isolator door 22. Such an assembly 52 can then, if necessary, be removed from the interior 18 of the isolator 16 and cleaned and then reinserted and repositioned in the region adjacent to the isolator opening 20.

The closure element line 44 has an outlet portion 64 which is preferably arranged above a collecting device, designated overall by the reference sign 56, for collecting the closure elements 12 that are transported into the interior 18 of the isolator. In the simplest case, the collecting device 56 is a bowl-shaped vessel which can preferably be shaken so that the closure elements 12 are aligned in a preferred position and can be gripped by a preferably automated (manufacturing) manipulation device, such that vessels arranged in the interior 18 of the isolator 16 can be closed in a manner known per se.

The actuator 38 is preferably connected to a control unit (not shown), by means of which a target quantity of closure elements 12 can be specified and which enables a comparison with a transported actual quantity of closure elements 12, this actual quantity being detected by means of the counting device 50. As long as a predetermined target quantity is less than a detected actual quantity of closure elements 12, the actuator 38 is controlled such that closure elements 12 can be conveyed into the closure element line 44 through an increase in the inclination a of the support surface 34. When the desired actual quantity is reached, the inclination of the support surface 34 is no longer increased or decreased.

To apply energy to closure elements 12 arranged in the receptacle 24, it is possible, in addition or as an alternative to the above embodiment described with reference to FIG. 1, that the support 32 interacts with an actuator 38 which changes the vibration state of the support 32 and thus also of the support surface 34 (see FIG. 2). This change in the vibration state is transmitted via the receptacle 24 to the closure elements 12 stored in the receptacle 24. For example, the actuator 38 can be designed as a vibrating linear conveyor, which vibrates the receptacle 24 and thus also the closure elements 12 stored therein, with at least one movement component of the vibration, starting from the receptacle 24, being directed toward the bridging portion 58 of the closure element line 44.

Instead of a receptacle 24 in the form of a bag 26, as described with reference to FIGS. 1 and 2, it is also possible to use a receptacle 28 with solid receptacle walls (see FIG. 3). Such a receptacle 24 can also be placed in a state of greater inclination and/or in a vibrating state with the aid of an actuator 38.

It is preferred that the receptacle 28 has an annular membrane 60 which provides a flexible transition between a rim 62 of the receptacle 28 and an outer wall of the isolator 16 and which at the same time ensures that an interior of the receptacle 28 remains uncoupled from the environment 14 of the isolator 16 and that closure elements 12 stored therein are not contaminated.

It is possible, as shown with reference to the exemplary embodiments according to FIGS. 1 to 3, for the closure elements 12 to be transported from the bridging portion 58 of a closure element line 44 to the outlet portion 64 solely with the aid of gravity, in order in this way to fall into a collecting device 56. However, it is also possible for a conveyor unit 66 to be used along the transport path from the isolator opening 20 to the collecting device 56. Such conveyor units are described with reference to the following drawings. These conveyor units 66 can be provided alternatively or additionally to an actuator 38 described with reference to FIGS. 1 to 3.

Figure 4:
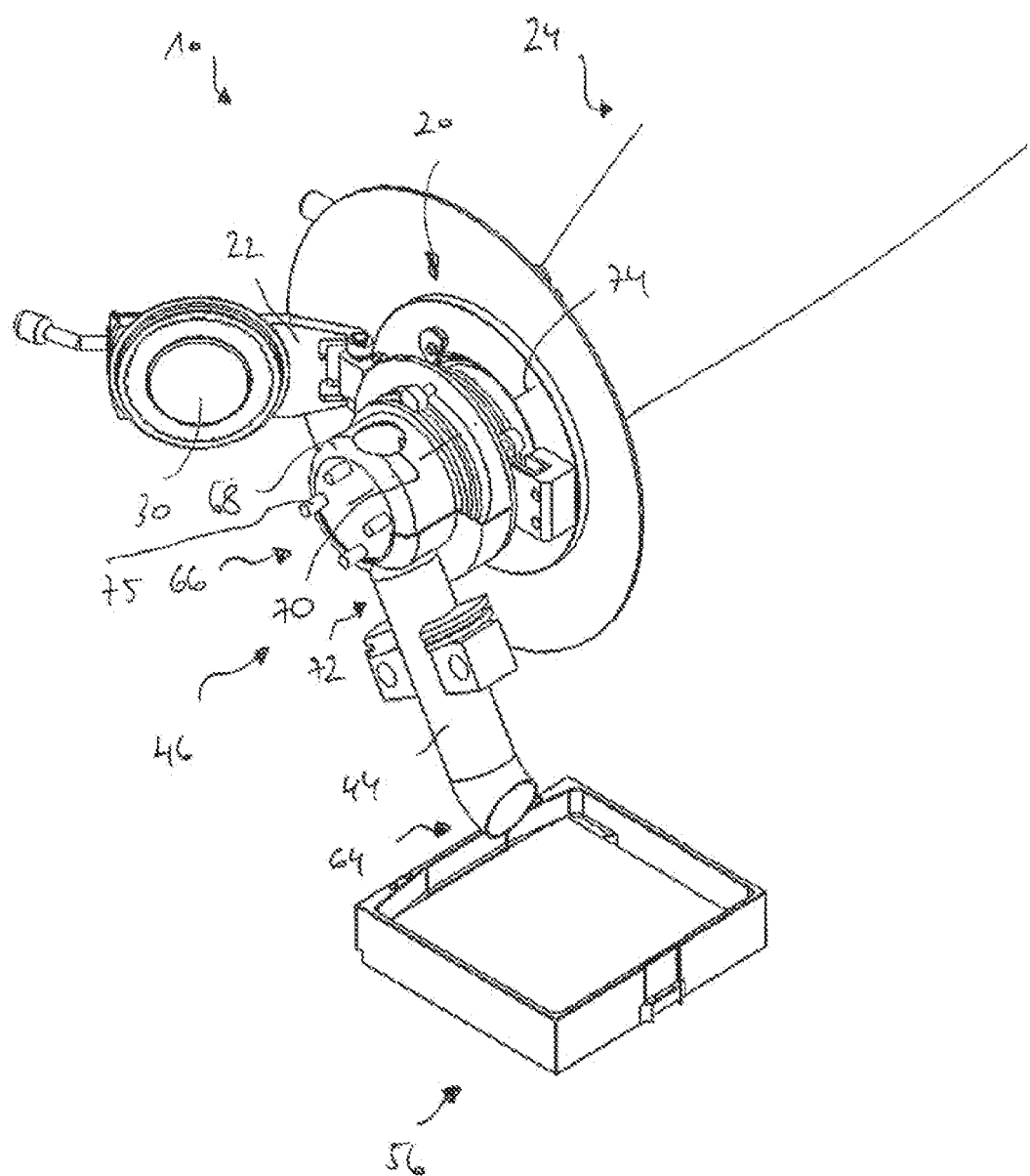
FIGS. 4 to 6 show perspective views of a further embodiment of a system for transporting loose sterile closure elements, the system comprising a conveyor device with a hollow-cone-shaped conveyor drum.
Figure 5:
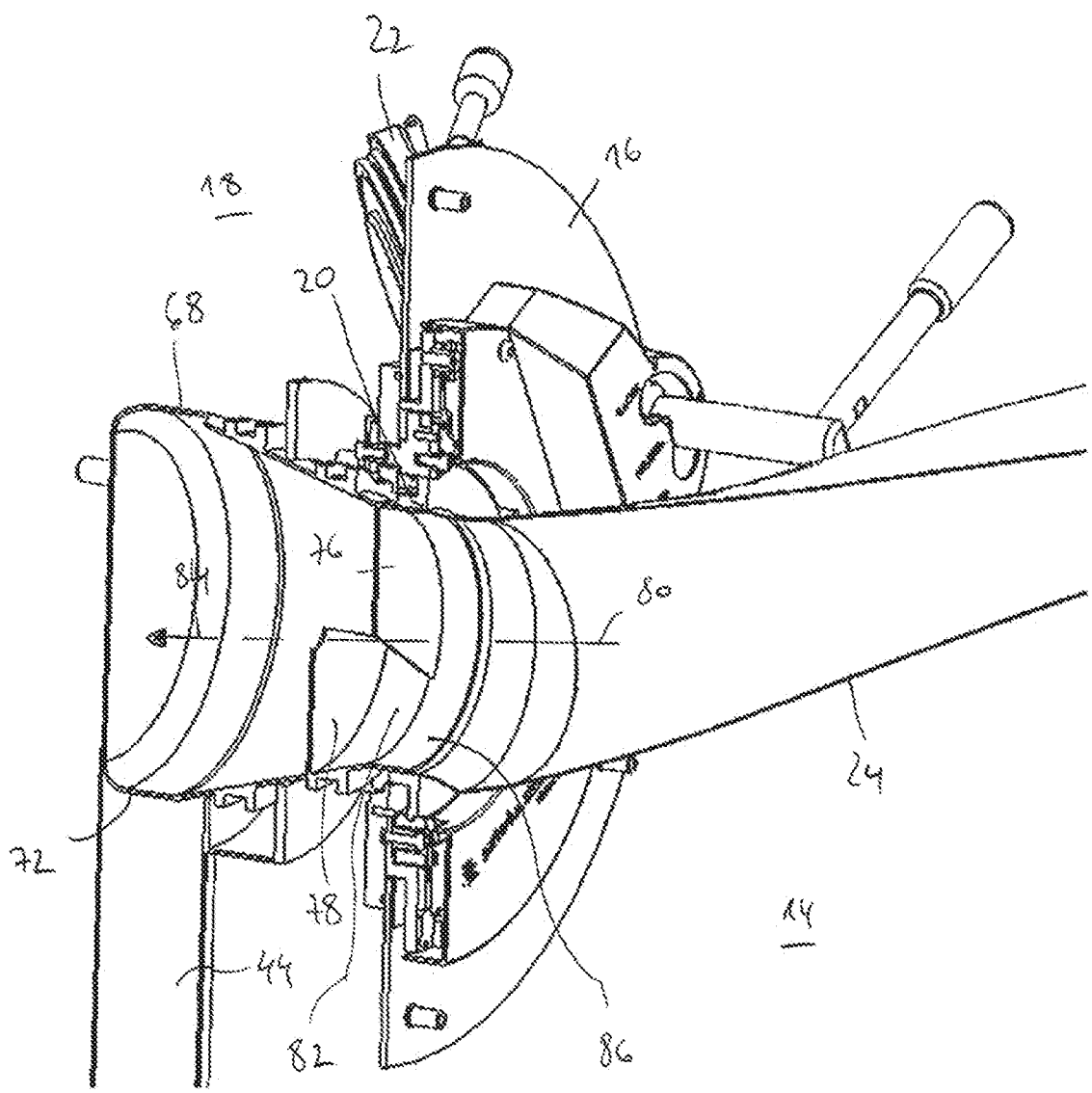
Figure 6:
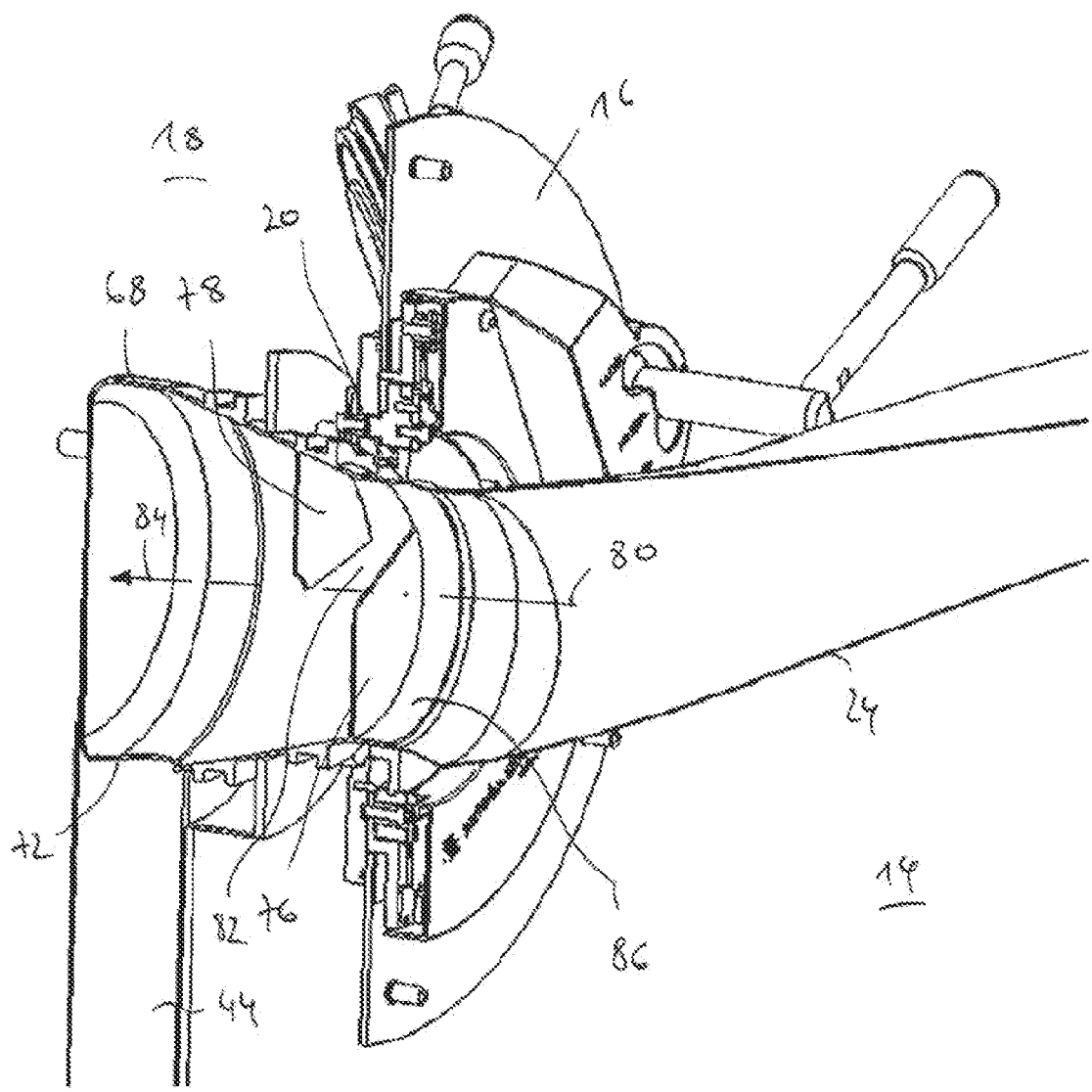

A conveyor unit 66 of the exemplary embodiment according to FIGS. 4 to 6 comprises a conveyor drum 68 with a drum opening 70 which can be brought into alignment with an input section 72 of a closure element line 44 downstream of the conveyor unit 66. For this purpose, the conveyor drum 68 can be driven to rotate about a central drum axis 74. A conveyor drive device (not shown), for example a motor, is provided for this purpose, which drives at least one drive element 75 of the conveyor drum 68 directly or via gear elements. Such drive elements 75 can, for example, have a peg shape.

The cross section of the drum opening 70 is larger than a maximum cross section of a closure element 12 and preferably smaller than a maximum cross section of two closure elements 12 arranged at the same height as seen in the transport direction.

Conveyor elements 76, 78 arranged inside the conveyor drum 68, and firmly connected to the conveyor drum 68, extend at an angle, in particular substantially perpendicularly, to a transport axis 80 of the closure elements 12. The conveyor elements 76, 78 can be designed, for example, as guide webs or guide plates. Viewed along the transport axis 80, the conveyor elements 76 and 78 delimit a conveyor chamber 82 which is outwardly delimited by an inner wall of the conveyor drum 68. The conveyor chamber 82 serves to convey individual closure elements 12 into the closure element line 44.

FIGS. 5 and 6 each show different sections of the conveyor elements 76 and 78 that complement one another, with the conveyor drum 68 in FIGS. 5 and 6 adopting positions rotated through 180° relative to one another about the drum axis 74.

Closure elements 12 to be transported from the receptacle 24 along the transport axis 80 follow a transport direction designated by reference sign 84 shown in FIGS. 5 and 6. Starting from the receptacle 24 and seen in the direction of transport 84, the conveyor drum 68 has a conveyor drum section 86. The conveyor drum section 86 bridges the door opening 20 between the receptacle 24 arranged in the environment 14 and the interior 18 of the isolator 16.

In the region of the conveyor chamber 82, the conveyor drum 68 has an interior that widens in the shape of a hollow cone, as seen in the transport direction 84 (compare FIGS. 5 and 6).

Figure 7:
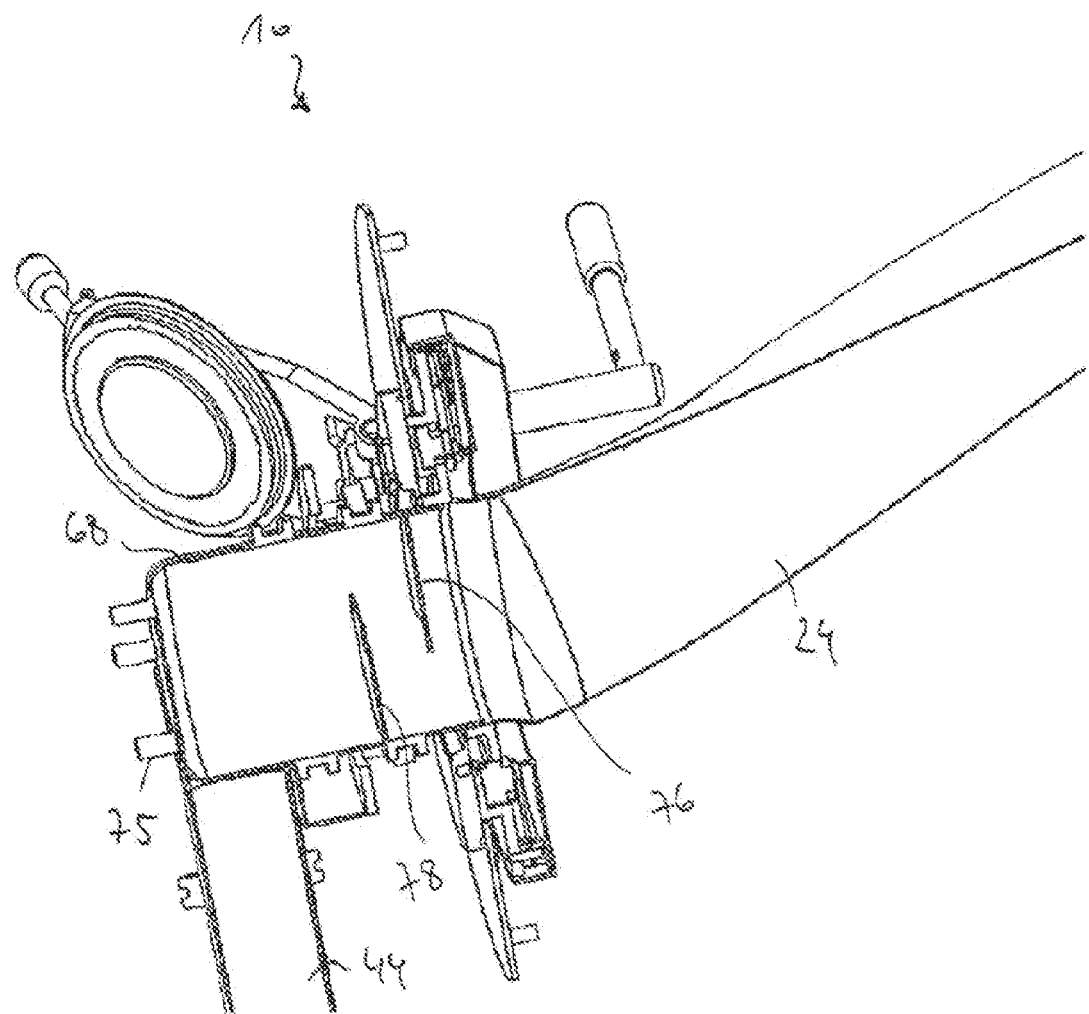
FIGS. 7 and 8 show perspective views of a further embodiment of a system for transporting loose sterile closure elements, the system comprising a conveyor device with a hollow-cylindrical conveyor drum.
Figure 8:
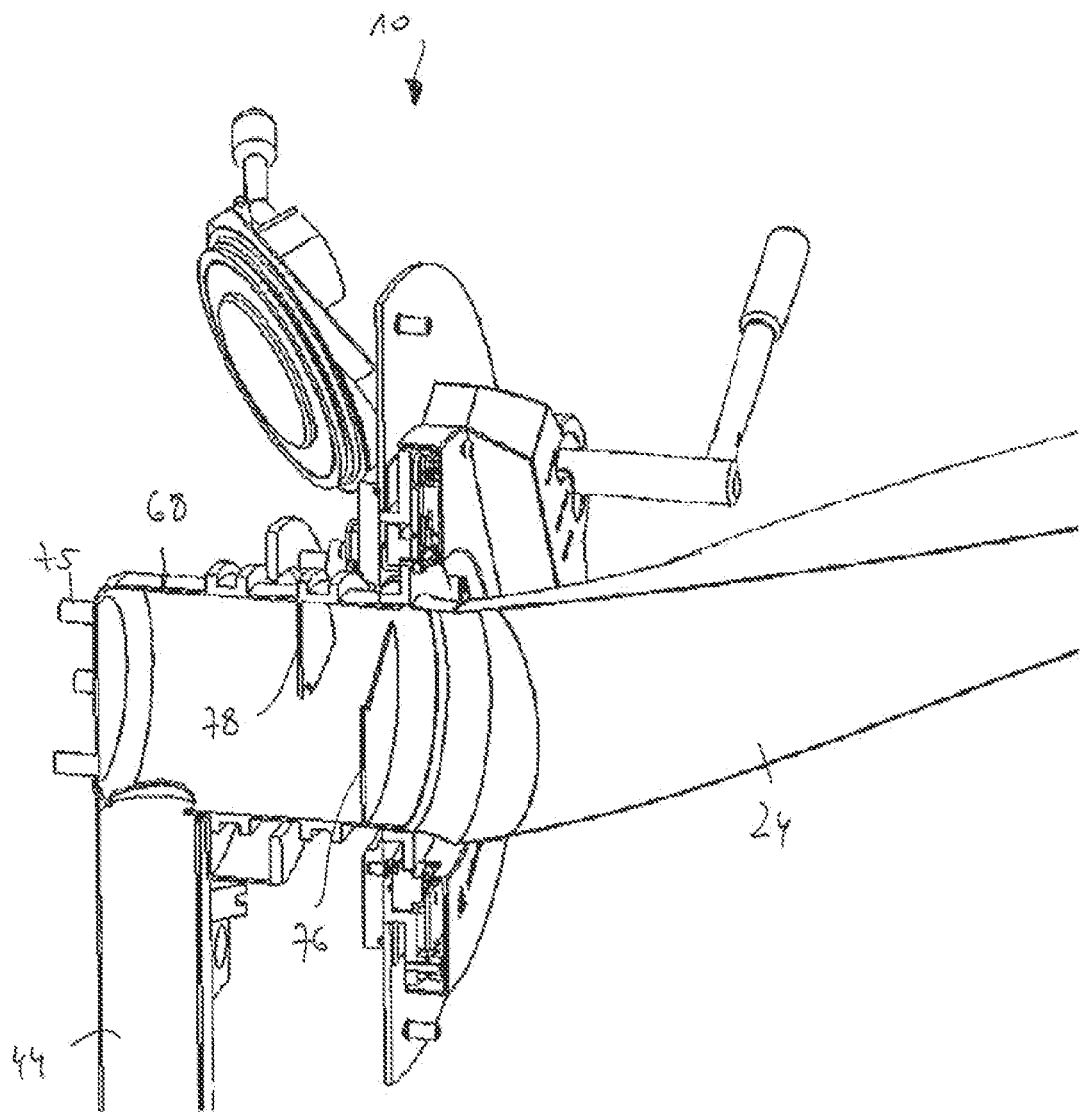

As an alternative to a conveyor drum 68 that widens in the shape of a hollow cone, a cylindrical drum 68 can also be used (see FIGS. 7 and 8). Otherwise, for the exemplary embodiment according to FIGS. 7 and 8, reference is made to the above description of the exemplary embodiment of FIGS. 4 to 6.

Figure 9:
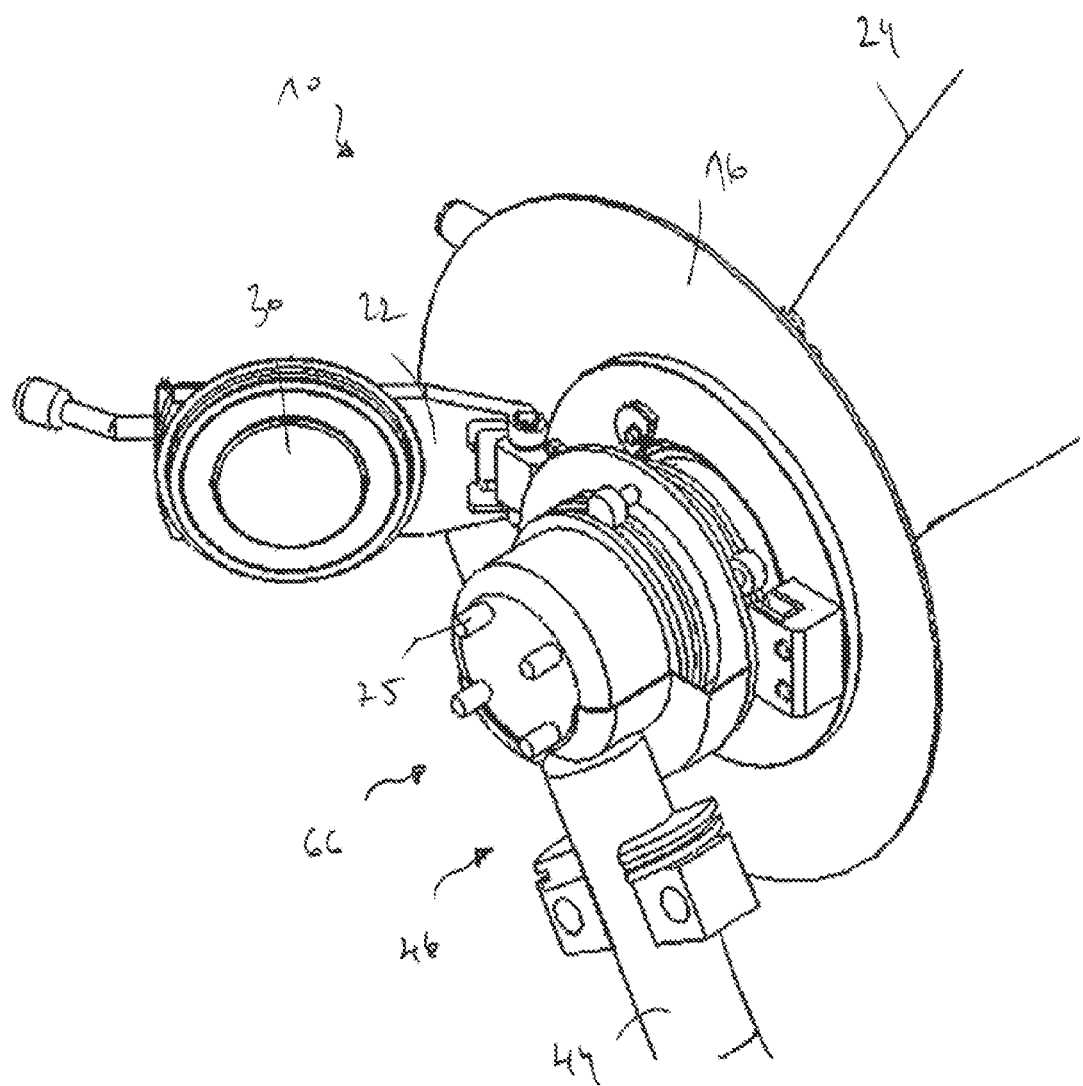
FIGS. 9 and 10 show perspective views of a further embodiment of a system for transporting loose sterile closure elements, the system comprising a conveyor device with a screw-shaped conveyor element which can be driven together with a conveyor drum.
Figure 10:
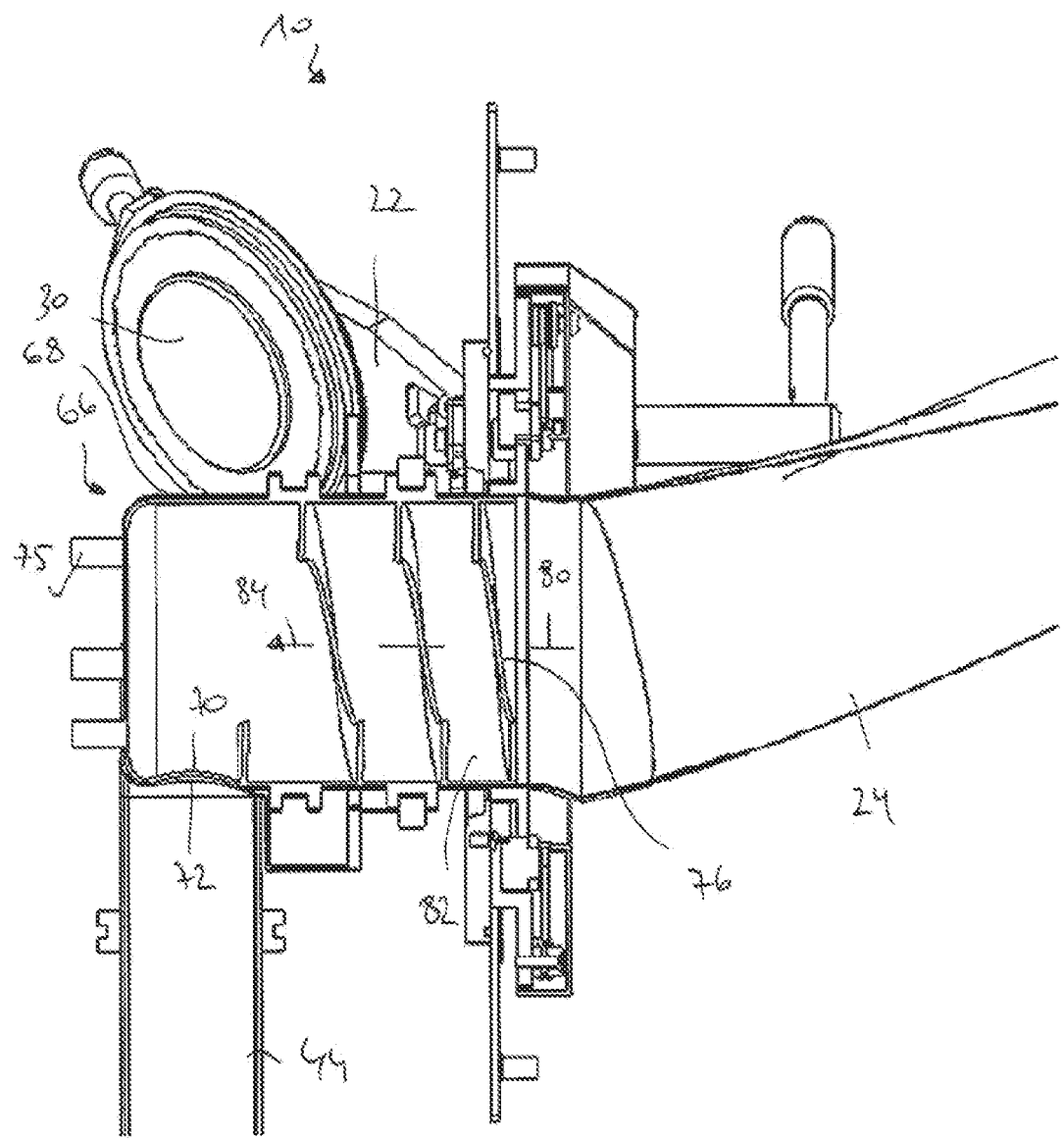

An exemplary embodiment shown in FIGS. 9 and 10 differs from the embodiments shown with reference to FIGS. 4 to 8 in that a conveyor element 76 is provided in the form of a screw conveyor. The conveyor element 76 is connected for conjoint rotation to the conveyor drum 68, which is in particular of cylindrical shape. The pitch of the helical conveyor element 76 preferably increases as seen in the direction of transport 84 of the closure elements 12, such that a volume of the conveyor chamber 82 increases as seen in the direction of transport 84.

In the exemplary embodiments according to FIGS. 4 to 10, the conveyor drive device (not shown) drives the at least one drive section 75 of the conveyor unit 66, such that both the conveyor drum 68 and the conveyor elements 76, 78 arranged in the conveyor drum 68 are rotated about the drum axis 74.

Figure 11:
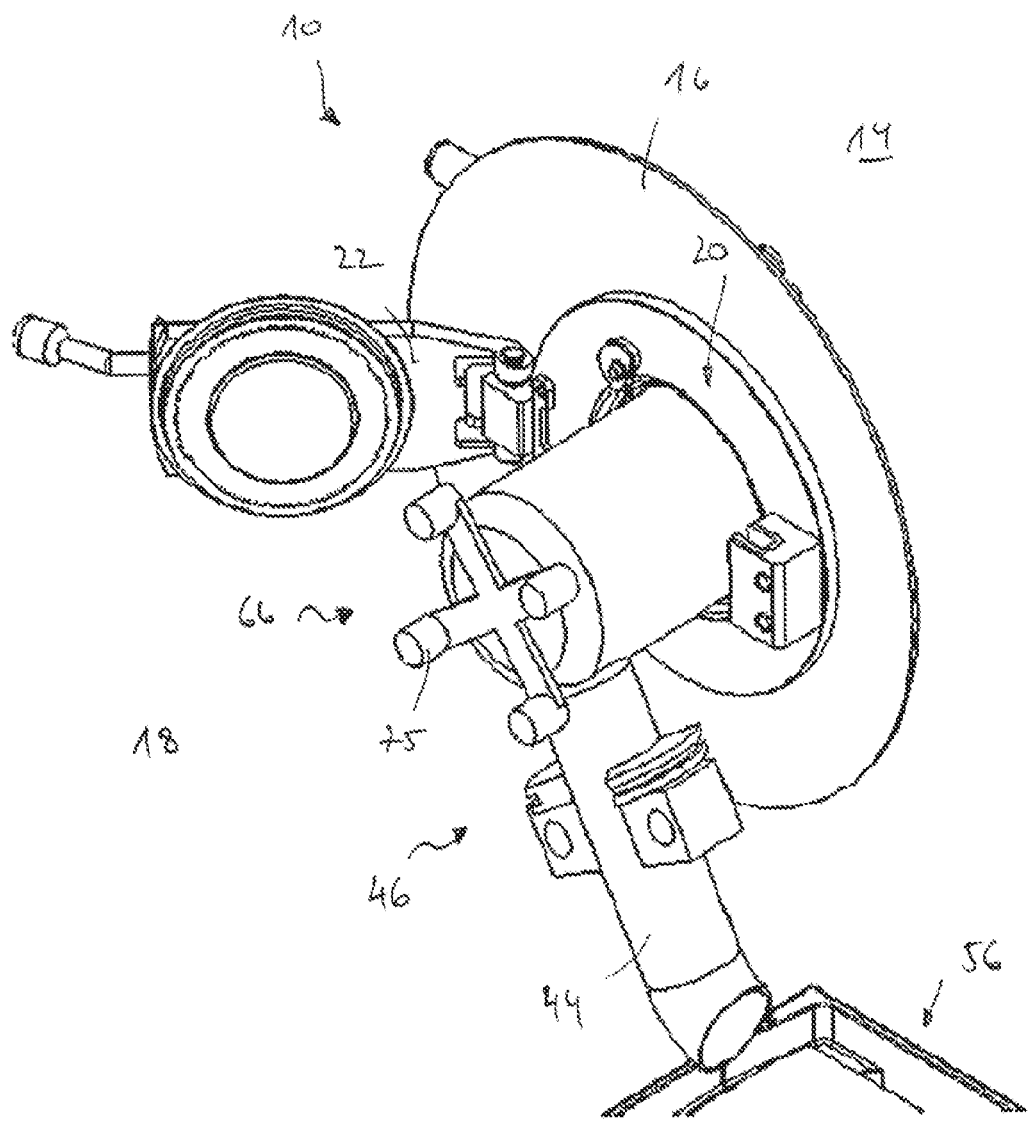
FIGS. 11 and 12 show perspective views of a further embodiment of a system for transporting loose sterile closure elements, the system comprising a conveyor device with a screw-shaped conveyor element which can be driven independently of a conveyor drum.
Figure 12:
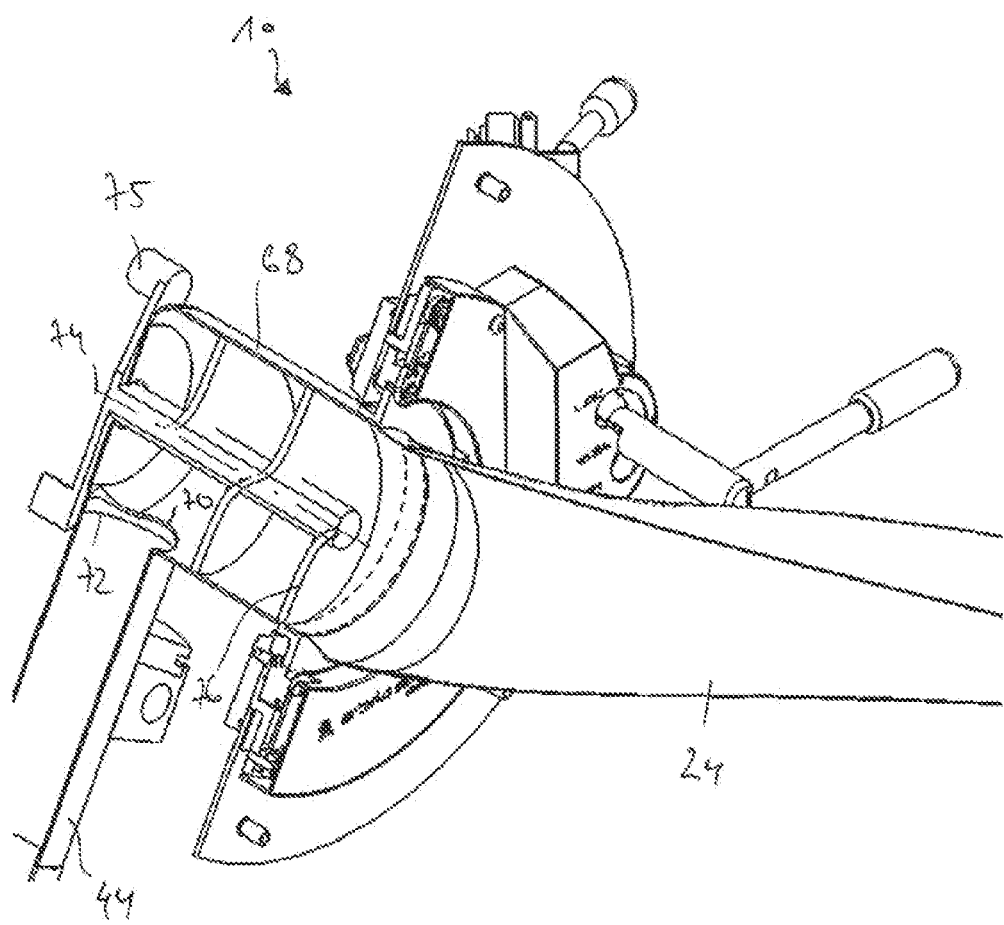

As an alternative, a fixed conveyor drum 68 can also be used (see FIGS. 11 and 12), the at least one drive section 75 interacting only with at least one conveyor element 76 and not with the conveyor drum 68. In other words, at least one conveyor element 76 is rotated about a stationary drum axis 74 of a stationary conveyor drum 68. Such an arrangement is particularly suitable for conveyor elements 76 in the form of a conveyor screw or spiral.

Figure 13:
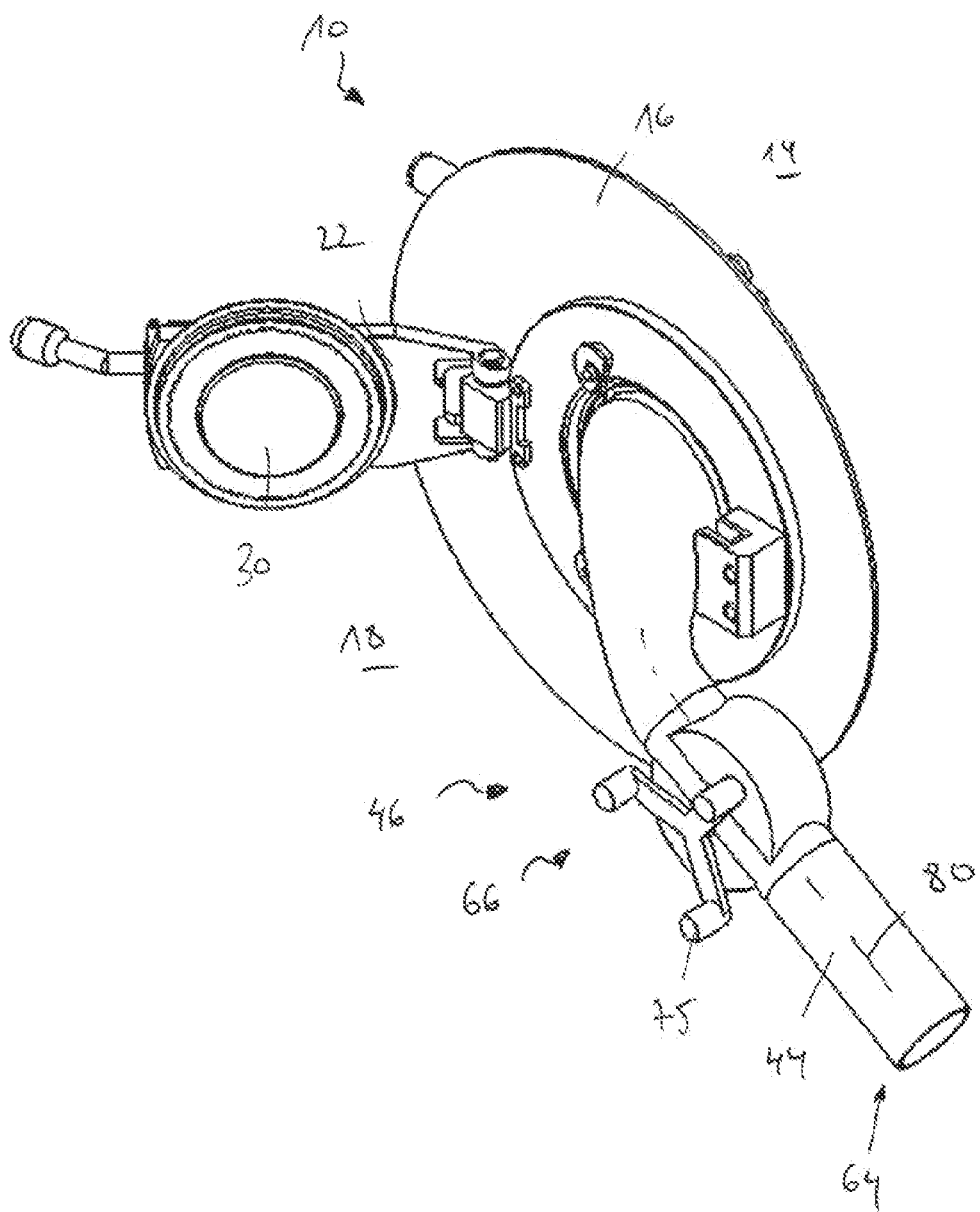
FIGS. 13 and 14 show perspective views of a further embodiment of a system for transporting loose sterile closure elements, the system comprising a conveyor device with a conveyor element in the form of a star wheel.
Figure 14:
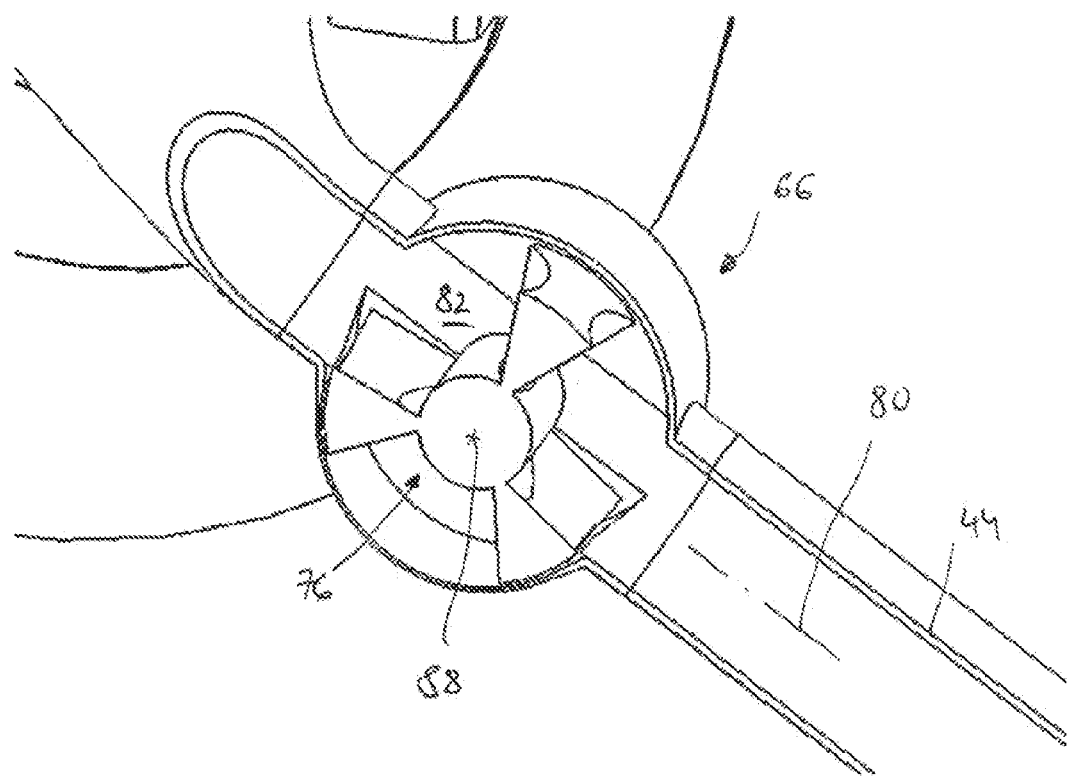

In the exemplary embodiments described above with reference to FIGS. 4 to 12, an axis of rotation of the conveyor unit 66 runs at least substantially parallel to a transport axis 80 of the closure elements 12. Deviating from this, FIGS. 13 and 14 show an exemplary embodiment of a system 10 with a conveyor unit 66 whose axis of rotation 88 runs perpendicular to a transport axis 80 of the closure elements 12. The conveyor element 76 of the conveyor unit 66 of the system 10 according to FIGS. 13 and 14 is designed as a conveyor wheel, which can be driven in rotation in the above-described manner via at least one drive section 75.

Figure 15:
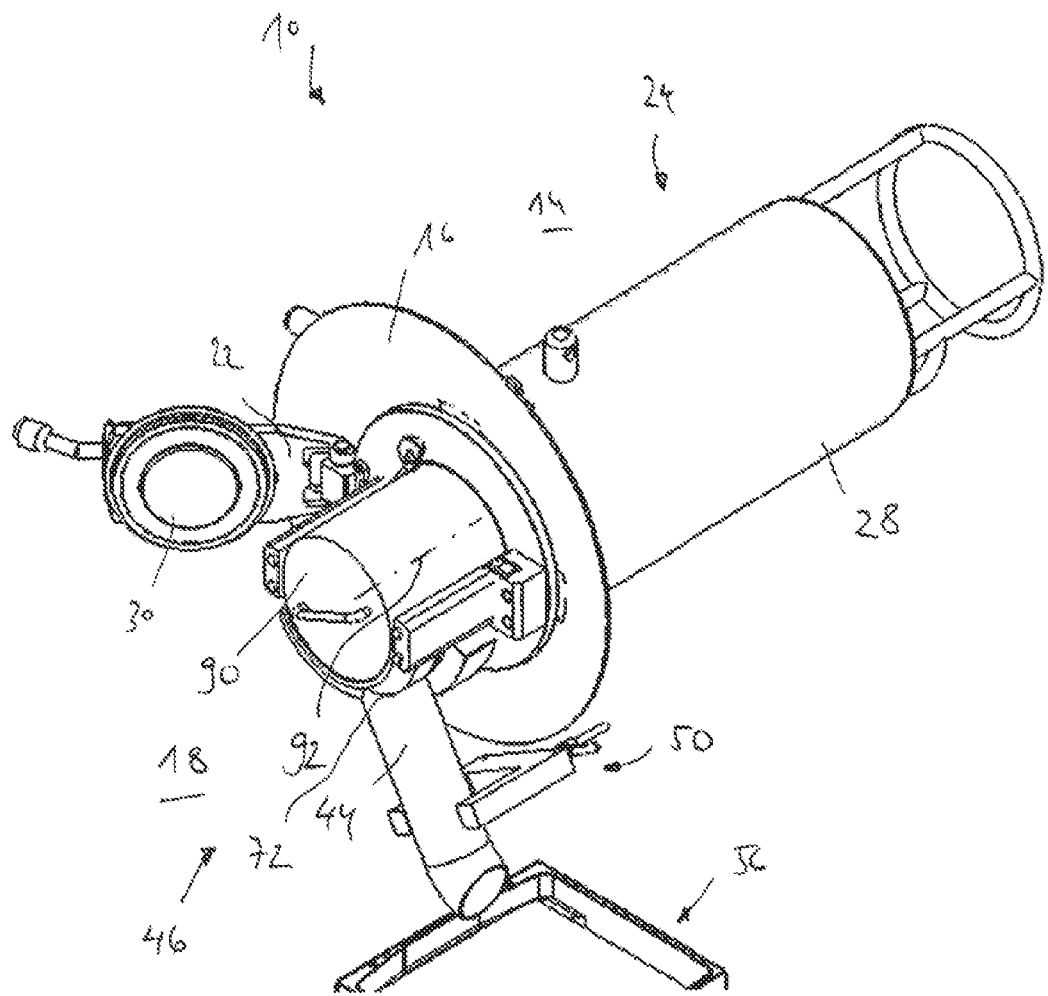
FIG. 15 shows a perspective view of a further embodiment of a system for transporting loose sterile closure elements, the system comprising a receptacle in the form of a container which has a rotatable section.

FIG. 15 shows a system 10 suitable for receptacles 24 in the form of a container 28. The container 28 has an extension piece 90 which, when the receptacle 24 is arranged on an isolator 16, is displaceable from the environment 14 of the isolator 16 into the interior 18 of the isolator 16. The extension piece 90 is also rotatable about a central receptacle axis 92 by means of a receptacle drive device (not shown). The extension piece 90 has an opening (not shown) which corresponds to an opening 70 of a conveyor drum 68 (see FIG. 12 for example). This opening can be brought into alignment with an inlet section 72 of a closure element line 44, as a result of which closure elements 12 pass from the receptacle 24 via the interior of the extension piece 90 into the closure element line 44 and are fed to a collecting device 56.

What is claimed is:

1. A system (10) for transporting loose sterile closure elements (12) from an environment (14) of an isolator (16) into an interior (18) of the isolator (16), comprising a receptacle (24) for storing a stock quantity of closure elements (12) in the environment (14) of the isolator (16), an isolator opening (20), and a collecting device (56) for collecting the closure elements (12) and for providing the closure elements (12) in the interior (18) of the isolator (16), and further comprising a metering device (46) for controlling a target quantity of closure elements (12) to be transported from the receptacle (24) through the isolator opening (20) and into the collecting device (56), and
   wherein the metering device (46) comprises at least one conveyor unit (66) with a conveyor chamber (82) whose volume is greater than a volume of an individual closure element (12).

2. The system (10) as claimed in claim 1, wherein the metering device (46) has at least one actuator (38) which can be switched between a resting state and a use state depending on the target quantity to be transported.

3. The system (10) as claimed in claim 2, wherein the use state is associated with an increase in potential and/or kinetic energy at least of a subset of the stock quantity of the closure elements (12).

4. The system (10) as claimed in claim 2, wherein a support (32) arranged in the environment (14) of the isolator (16) is provided for the receptacle (24), the at least one actuator (38) changing an inclination and/or a vibrational state of the support (32) and of the receptacle (24).

5. The system (10) as claimed in claim 1, wherein the receptacle (24) is configured as a bag (26) or as a container (28).

6. The system (10) as claimed in claim 1, wherein the conveyor unit (66) has a conveyor drum (68) which forms an outer boundary of the conveyor chamber (82) relative to a transport axis (80) of the closure elements (12).

7. The system (10) as claimed in claim 6, wherein the conveyor drum (68), relative to the transport axis (80) of the closure elements (12), has a hollow-cylindrical portion and/or widens in the form of a hollow cone as seen in a transport direction (84) of the closure elements (12).

8. The system (10) as claimed in claim 1, wherein the conveyor unit (66) has at least one conveyor element (76, 78) which delimits the conveyor chamber (82) as seen along a transport axis (80) of the closure elements (12).

9. The system (10) as claimed in claim 6, wherein the metering device (46) comprises a conveyor drive device, which can be switched depending on the target quantity to be transported, for rotating the conveyor drum (68) and/or conveyor elements (76, 78).

10. The system (10) as claimed in claim 1, wherein the metering device (46) comprises a receptacle drive device for rotating the receptacle (24) or a section of the receptacle (24) about a central receptacle axis.

11. The system (10) as claimed in claim 1, wherein the metering device (46) comprises a closure element line (44) which has a bridging portion (58) arranged within the isolator opening (20).

12. The system (10) as claimed in claim 1, wherein the metering device (46) comprises a counting device (50) for detecting a number, a weight and/or a volume of the closure elements (12).

13. The system (10) as claimed in claim 1, wherein the metering device (46) or parts of the metering device (46) is or are provided as an assembly (52) that is movable within the isolator (16).

14. The system (10) as claimed in claim 13, wherein the assembly (52) is movable by a robot arm.

15. The system (10) as claimed in claim 1, wherein no buffer store for closure elements (12) is connected upstream of the collecting device (56) within the isolator (16).

16. The system (10) as claimed in claim 1, wherein the volume of the conveyor chamber (82) is smaller than a volume of two closure elements (12).

17. The system (10) as claimed in claim 16, wherein the conveyor unit (66) is used along a transport path from the isolator opening (20) to the collecting device (56).

18. The system (10) as claimed in claim 12, wherein the counting device (50) is arranged upstream of the collecting device (56) as seen in a transport direction of the closure elements (12).

\* \* \* \* \*